US009751742B2

(12) United States Patent
Hayakawa et al.

(10) Patent No.: US 9,751,742 B2
(45) Date of Patent: Sep. 5, 2017

(54) DRINK FILLING SYSTEM AND STERILIZING METHOD THEREOF

(71) Applicant: DAI NIPPON PRINTING CO., LTD., Tokyo (JP)

(72) Inventors: Atsushi Hayakawa, Tokyo (JP); Shuta Ito, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 49 days.

(21) Appl. No.: 14/646,552

(22) PCT Filed: Dec. 17, 2013

(86) PCT No.: PCT/JP2013/083698

§ 371 (c)(1),
(2) Date: May 21, 2015

(87) PCT Pub. No.: WO2014/103787

PCT Pub. Date: Jul. 3, 2014

(65) Prior Publication Data

US 2015/0291406 A1 Oct. 15, 2015

(30) Foreign Application Priority Data

Dec. 27, 2012 (JP) ................................ 2012-284900
Jun. 26, 2013 (JP) ................................ 2013-133463

(51) Int. Cl.
*C02F 1/68* (2006.01)
*A61L 2/00* (2006.01)
(Continued)

(52) U.S. Cl.
CPC .............. *B67C 3/001* (2013.01); *B08B 9/027* (2013.01); *B08B 9/0325* (2013.01);
(Continued)

(58) Field of Classification Search
CPC ..... A61L 2/00; A61L 2/07; B08B 3/00; B08B 3/04
(Continued)

(56) References Cited

U.S. PATENT DOCUMENTS

2008/0142439 A1* 6/2008 Berglof .................... A61L 2/04 210/636
2010/0074816 A1 3/2010 Nakano et al.
2011/0265820 A1 11/2011 Dahlberg et al.

FOREIGN PATENT DOCUMENTS

JP 61-092555 A 5/1986
JP 2000-070344 A 3/2000
(Continued)

OTHER PUBLICATIONS

J. Kao, et al.; "Thermal Process Calculations for Different Z and jc Values Using a Hand-Held Calculator", Journal of Food Science, vol. 47; Issue 1, pp. 193-197; Jan. 1982; XP-002759013.*
(Continued)

*Primary Examiner* — Monzer R Chorbaji
(74) *Attorney, Agent, or Firm* — Ladas & Parry LLP

(57) ABSTRACT

In a sterilizing method for a drink filling system provided with a drink supply pipe line (7) for feeding drink into a filling machine (2) through a heating sterilizing section (18), wherein hot water or heated steam is fed to the drink supply pipe line (7), F-values are calculated while detecting temperature at a plurality portions of the drink supply pipe line at every predetermined time interval, and a sterilizing process is ended at a time when a minimum F-value reaches an aimed value. According to such method, a working time till the starting of drink filling work or a producing interval time can be shortened.

3 Claims, 5 Drawing Sheets

(51) Int. Cl.
*B67C 3/00* (2006.01)
*B08B 9/032* (2006.01)
*B67C 7/00* (2006.01)
*B08B 9/027* (2006.01)

(52) U.S. Cl.
CPC ........ *B67C 7/0073* (2013.01); *B08B 2230/01* (2013.01); *B65B 2210/06* (2013.01); *B65B 2210/08* (2013.01)

(58) Field of Classification Search
USPC ................... 422/1, 26, 38, 292; 210/748.01; 134/22.12, 22.15, 22.18, 30
See application file for complete search history.

(56) References Cited

FOREIGN PATENT DOCUMENTS

| | | | |
|---|---|---|---|
| JP | 2000-1532453 | A | 6/2000 |
| JP | 2007-022600 | A | 2/2007 |
| JP | 2007-215893 | A | 8/2007 |
| JP | 2007-331801 | A | 12/2007 |

OTHER PUBLICATIONS

J. Kao, et al; “Thermal Process Calculations for Different z and jc Values Using a Hand-Held Calculator”, Journal of Food Science, vol. 47; Issue 1, pp. 193-197; Jan. 1982, XP-002759013.

International Search Report mailed Apr. 1, 2014; PCT/JP2013/083698.

“WaveResearcher for Windows”, Darwi/HR Ver. 3.0; Habilis Corporation (Darwin-V3MGA1 Jul. 2006; 10 Pages.

* cited by examiner

DRINK FILLING SYSTEM AND STERILIZING METHOD THEREOF

TECHNICAL FIELD

The present invention relates to a system for filling a container such as PET bottle with a drink and a method of sterilizing the drink filling system.

BACKGROUND TECHNOLOGY

When it is required to fill a container such as bottle with a drink from an aseptic drink filling machine, it is of course not only necessary to sterilize a drink itself so as to keep an aseptic condition, but also necessary to preliminarily clean an interior of a drink supply pipe line provided with a surge tank, a liquid feed pipe, a drink filling nozzle and so on of the aseptic drink filling machine and then sterilize the drink supply pipe line so as to create and keep an aseptic condition.

In a known technology, an F-value as a sterilization value to the drink itself passing through the interior of a drink filling path has been measured so as to confirm whether it is worth while for the drink to receive quality guarantee or not based on history information thereof (for example, see Patent Document 4).

In addition, for the drink supply pipe line of the aseptic drink filling machine, a CIP (Cleaning In Place) treatment and an SIP (Sterilizing In Place) treatment have been performed at every time when a kind of a drink is periodically changed (for example, see Patent Documents 1, 2 and 3).

The CIP treatment is performed, for example, by flowing a cleaning liquid prepared with water to which alkaline chemical agent such as caustic soda is added in a flow path from an inside of a pipe line of a drink filling path to a filling nozzle of a filling machine, and thereafter, by filling a cleaning liquid prepared with water to which acidic chemical agent is added. According to such treatment, remaining content of previously filled drink adhering to the drink filling path can be removed (see, for example, Patent Documents 1, 2, and 3).

The SIP treatment is a treatment for preliminarily sterilize the interior of the drink supply pipe line before drink filling working, and for example, this SIP treatment is performed, for example, by circulating steam or heated water through the drink filling path cleaned by the CIP treatment mentioned above. According to such treatment, the interior of the drink filling path can be sterilized to thereby provide an aseptic condition (see, for example, paragraph [0003] of Patent Document 3).

PRIOR ART DOCUMENT

Patent Document

Patent Document 1: Japanese Patent Laid-open Publication No. 2007-331801

Patent Document 2: Japanese Patent Laid-open Publication No. 2000-153245

Patent Document 3: Japanese Patent Laid-open Publication No. 2007-22600

Patent Document 4: Japanese Patent Laid-open Publication No. 2007-215893

SUMMARY OF THE INVENTION

Problem to be Solved by the Invention

In a conventional technology concerning products of drink and food, a sever F-value control has been carried out because of change in quality such as taste and the like of the drink and food products themselves based on short-and-long heating time therefor.

However, since a drink supply pipe line of an aseptic drink filling system is constructed mainly of metal material such as stainless steel member, the quality of a drink is hardly changed, and accordingly, F-value has been relatively roughly controlled.

For example, when a heating treatment is preformed at a temperature of 130° C. for 30 minutes, the F-value is 233, and it has been known in experience that such F-value has no problem for performing the sterilizing treatment to a drink supply pipe line. Based in such knowledge, temperatures at portions, at which the temperatures of the drink supply pipe line are difficult to be increased while flowing heated steam or hot water within the drink supply pipe line, are measured by temperature sensors, and when the temperatures at these portions reach 130° C., a timer operates, and after elapse of 30 minutes of the timer, the heating treatment by the heated steam or like to the drink supply pipe line is ended.

FIG. 6 is a graph representing a heating method for the drink supply pipe line using a relationship between temperature and time. That is, the drink supply pipe line starts to be heated by feeding steam or like for 30 minutes from a point time at which a lowest temperature among the temperatures measured by the temperature sensors disposed for the various portions of the drink supply pipe line, and after 30 minutes passed, the supply of the steam or like is stopped. Thereafter, instead of the steam or like, an aseptic cooling wind or like is supplied to cool the interior of the drink supply pipe line. In FIG. 6, the reason why the temperature is increased to 135° C. resides in safeness in temperature change. In FIG. 6, a condition for the sterilization resides in indication of the temperature of more than 130° C. for 30 minutes, and the hatched area (portion) corresponds to the F-value of 233. However, in actual, an integrated area (portion) of the F-value of a portion over the temperature of 130° C. is ignored.

However, in accordance with recent requirement of small energy consumption, attention has been paid to largeness of heat energy consumed for an SIP treatment, as well as length of time required for the SIP treatment in viewpoint of productivity of drink.

Therefore, in order to solve the problems mentioned above, an object of the present invention is to provide a drink filling system and a sterilizing method therefor.

Means for Solving the Problems

The inventors of the present invention studied and checked an F-value control and management for rethinking the heating energy and sterilizing time required for an SIP (Sterilizing In Place) treatment, and they found out that the F-value reaches the value of 233 for a time less than 30 minutes because, by controlling sterilizing effect based on integration with the F-value in addition to mere the control of the time after reaching 130° C., the F-value integration from 121.1° C. to 130° C. and the F-value integration over 130° C. can be controlled.

The present invention has been conceived on the basis of the above finding and is characterized by the following configurations.

It is further to be noted that although the description is made with parentheses to reference numerals in figures, the present invention is not limited thereto.

That is, the invention according to claim 1 adopts a sterilizing method for a drink filling system provided with a drink supply pipe line (7) for feeding drink into a filling machine (2) through a heating sterilizing section (18), wherein hot water or heated steam is fed to the drink supply pipe line (7), F-values are calculated while detecting temperatures at a plurality portions of the drink supply pipe line (7) at every predetermined time interval, and a sterilizing process is ended at a time when a minimum F-value reaches an aimed value.

As recited in claim 2, in the sterilizing method for a drink filling system according to claim 1, it may be desired that an upstream side return path (6) is provided for the upstream side pipe line section (7*a*) going through the heating sterilizing section (18) of the drink supply pipe line (7) to thereby form an upstream side circulation path, the F-values are calculated while flowing the hot water to the upstream side pipe line section (7*a*) and the F-values are also calculated while flowing the heated steam to the downstream side pipe line section (7*b*) extending from the downstream side of the upstream side pipe line section (7*a*) toward the inside of the filling machine, and the sterilizing process is ended at a time when each of the minimum F-values reaches the aimed valve.

As recited in claim 3, in the sterilizing method for a drink filling system according to claim 1 or 2, it may be desired that the F-value is calculated by using a following equation 1.

$$F=\int_{t_0}^{t_1} 10^{(T-Tr)/Z}dt \quad \text{[Equation 1]}$$

(wherein T is an optional sterilizing temperature (° C.), $10^{(T-Tr)/Z}$ is a fatality rate at the optional temperature T, Tr is a reference temperature (° C.), and Z is Z-value (° C.).)

For this equation, if the temperature T is constant and the heating is performed for $t_T$ minutes, the F-value will be expressed as:

$$F=t_T\times 10^{(T-Tr)/Z} \quad \text{[Equation 2]}$$

Effects of the Invention

According to the present invention, in the SIP treatment of the drink supply pipe line (7) of the drink filling system, the accumulation of the F-value is started at an early stage, and when the F-value reaches the aimed value, the sterilizing process is ended, so that the aseptic treatment can be achieved more accurately and speedily than that in a conventional technology. Therefore, amount of the hot water or heated steam to be used for the sterilization of the drink supply pipe line (7) can be reduced, and hence, the drink filling working can be started speedily in an early stage, and a production time interval for changing the drink can be shortened, thereby improving the production efficiency.

EMBODIMENT FOR CARRYING OUT THE INVENTION

An embodiment of the present invention will be explained hereunder with reference to the accompanying drawings.

Hereunder, a configuration or structure of the drink filling system is first explained, and then, a sterilizing method of this system will be explained.

Figure 1:
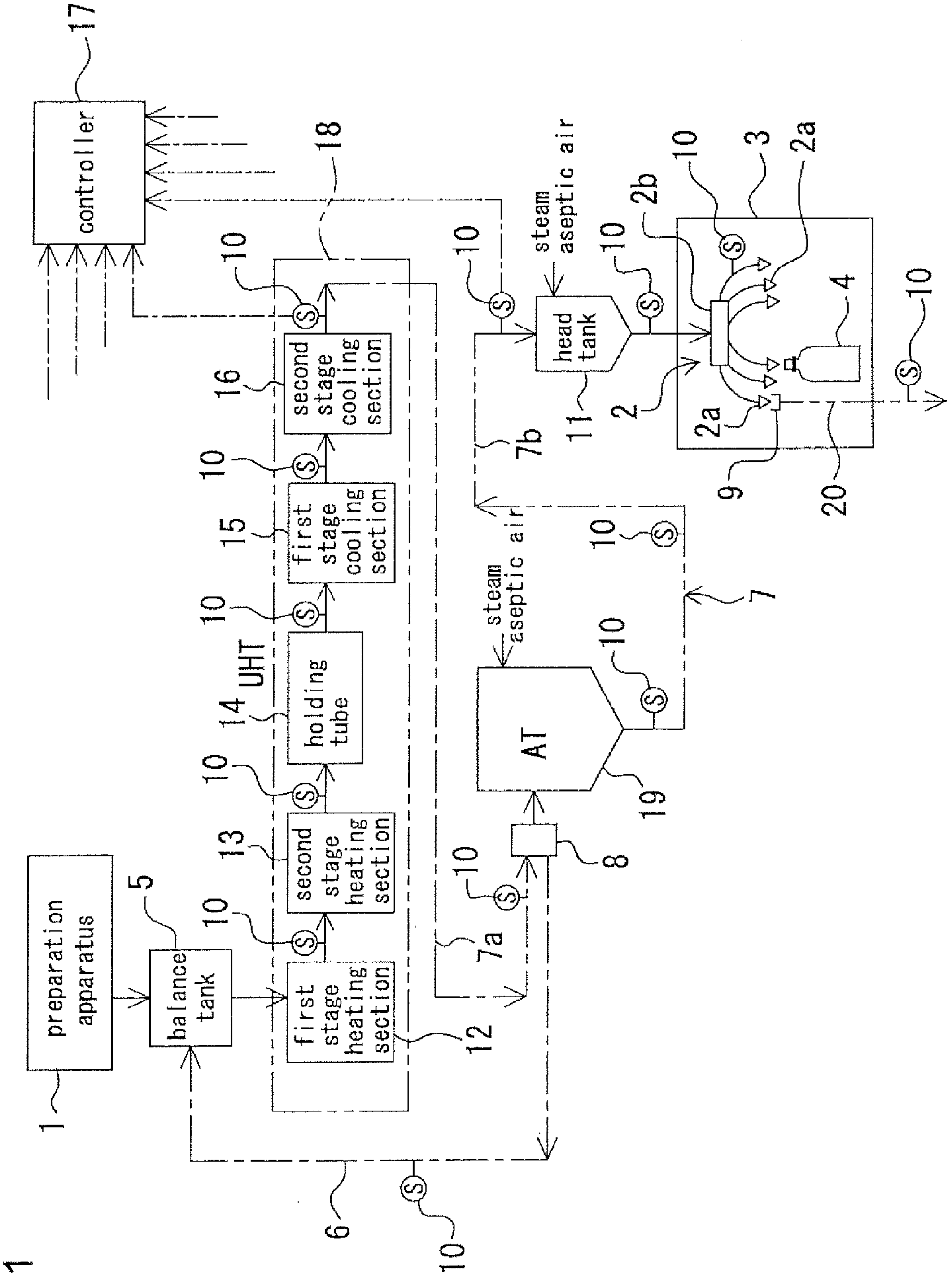
FIG. 1 is a block diagram showing a drink filling system according to the present invention.

As shown in FIG. 1, the drink filling system is provided with a drink preparation apparatus 1 and a filling machine 2 filling a bottle 4 with a drink. The drink preparation apparatus 1 and a filling nozzle 2*a* of the filling machine 2 are connected through a drink supply pipe line 7. Further, the filling machine 2 is surrounded by an aseptic chamber 3.

The preparation apparatus 1 is an apparatus for preparing, for example, tea drink, fruit drink and the like at a predetermined composition rate (blended rate), and since such preparation apparatus is known one, detailed explanation thereof is omitted herein.

The filling machine 2 is a machine provided with a wheel (not shown) that rotates a number of filling nozzles 2*a* at high speed in a horizontal plane, and this machine is for filling bottles 4 travelling in synchronism with a peripheral speed of the wheel disposed under the filling nozzles 2*a* with a constant amount of drink from the filling nozzles 2*a*, respectively, while rotating in conformity with the rotation of the wheel. Further, this filling machine 2 is also known one, and accordingly, detailed explanation thereof is omitted herein.

The drink supply pipe line 7 of the drink filling system is provided with a balance tank 5, a heat sterilizing section (UHT (Ultra High-Temperature) section) 18, a manifold valve 8, an aseptic tank 19, and a head tank 11 in this order from the upstream side toward the downstream side in view of the drink flow direction in the pipe line from the preparation apparatus 1 toward the filling machine 2.

The UHT section 18 is provided therein with a first stage heating section 12, a second stage heating section 13, a holding tube 14, a first stage cooling section 15, a second stage cooling section, and others and acts to gradually heat the drink or water supplied from the balance tank 5 while being delivered from the first stage heating section 12 to the second stage heating section 13, then heat the drink or water to an aiming temperature within the holding tube 14, and thereafter, cool the drink or water while cooling from the first stage cooling section to the second stage cooling section 16. The numbers of the heating sections and cooling sections may be changed as occasion demands.

Further, since the balance tank 5, the manifold valve 8, the aseptic tank 19, and the head tank 11 are all known ones, so that detailed explanations thereof are omitted herein.

Figure 2:
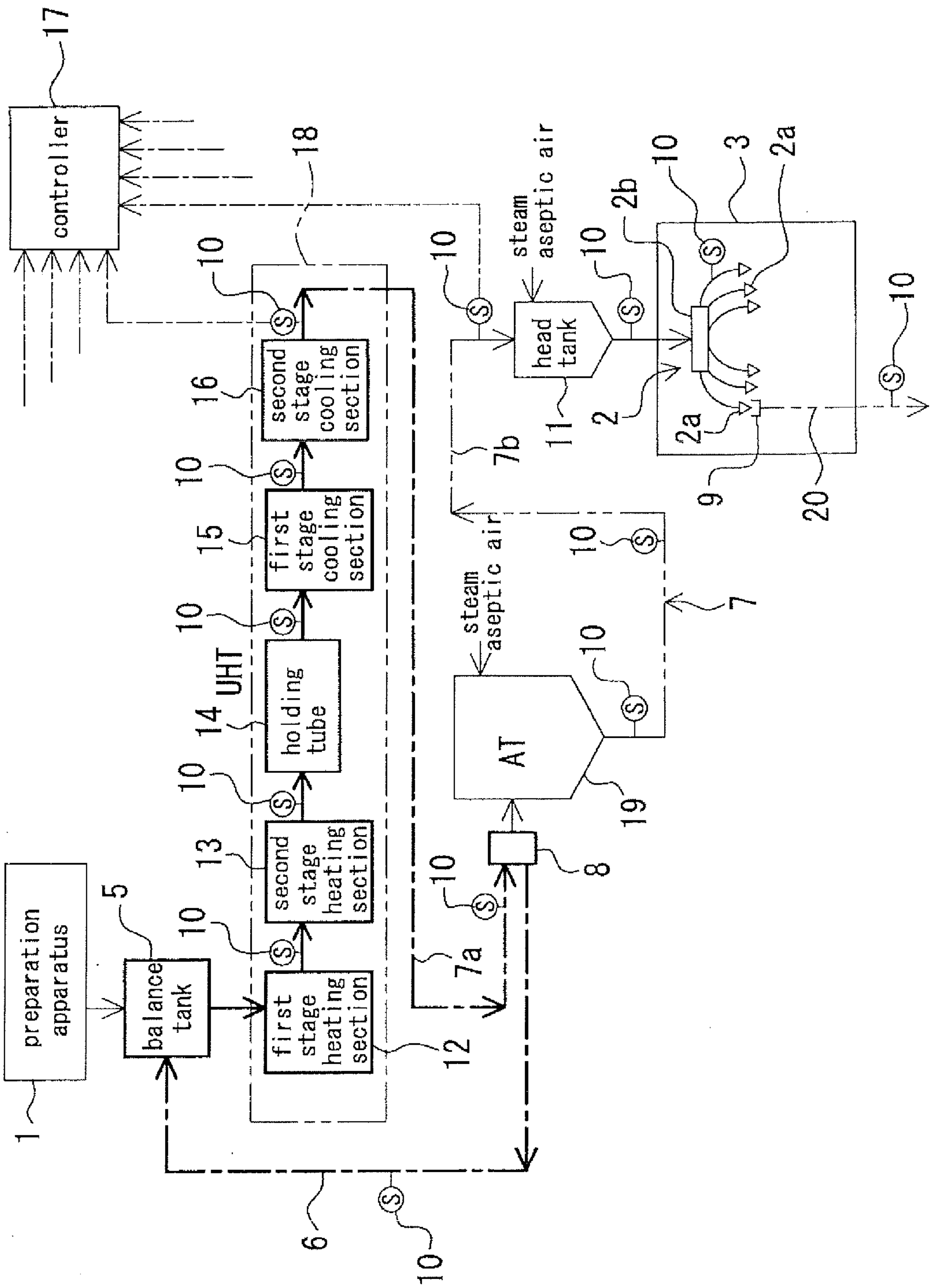
FIG. 2 is a block diagram showing a condition in which an SIP treatment is performed from a heat sterilizing section to a portion beforehand an aseptic tank (ACT) using a drink supply pipe line of the drink filling system.

As shown with a thick line in FIG. 2, an upstream side pipe line section 7*a* of the drink supplying pipe line 7 to the manifold valve 8 through the balance tank 5 and the UHT section 18 is provided with a return circulation path 6 to thereby constitute a circulation path for carrying out the SIP treatment.

Furthermore, the upstream side pipe line section 7*a* is provided with temperature sensors 10 at portions including a portion at which a temperature hardly increases at a time when hot water is supplied. These portions at which the temperature sensors 10 are arranged may include portions of the pipe line, for example, a portion between respective portions inside the UHT section 18, a portion just outside of the second stage cooling section 16, and a portion just before the manifold valve 8, and the temperature sensors 10 may be arranged to these portions, respectively. Informations of the temperatures measured at these portions by the respective temperature sensors 10 are sent to the controller 17.

Figure 3:
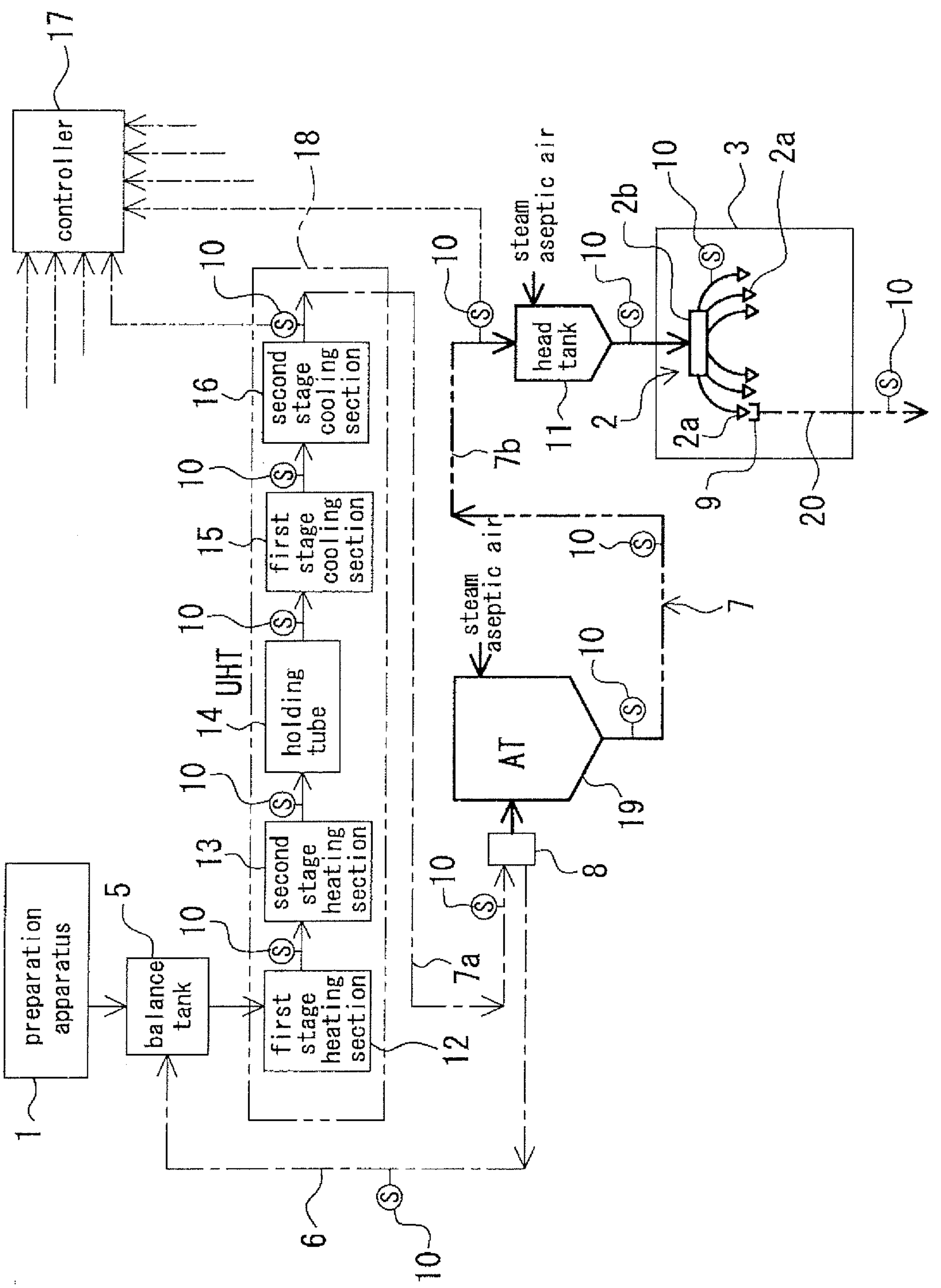
FIG. 3 is a block diagram showing a condition in which the SIP treatment is performed to a downstream side pipe line section extending from the aseptic tank (ACT) to a filling nozzle using the drink supply pipe line of the drink filling system.

As shown with the thick line in FIG. 3, such temperature sensors 10 may be also arranged at the downstream side pipe line section 7*b* extending from the manifold valve 8 disposed on the downstream side than the upstream side pipe line section 7*a* to the filling machine 2 through the aseptic tank 19 and the head tank 11 within the drink supply pipe line 7, and arranged specifically at respective portions including a portion at which the temperature hardly increases at a time when the heated steam is supplied. These portions at which the temperature sensors 10 are arranged may include portions of the pipe line, for example, a portion near the outlet port of the aseptic tank 11, a bent portion on the way of the pipe line, portions near inlet and outlet portions of the head tank 11, and a portion between the manifold 2*a* of the filling machine 2 and the filling nozzle 2*a*, and the temperature sensors 10 may be arranged to these portions, respectively, on the way of the pipe line. Informations of the temperatures measured at these portions by the respective temperature sensors 10 are sent to the controller 17.

Furthermore, on the downstream side of the pipe line section 7*b*, cups 9 which are able to approach or separate from the openings of the respective filling nozzles 2*a* of the filling machine 2 for the SIP treatment. At the time when the SIP treatment is performed, the respective cups 9 are applied to the front end openings of the filling nozzles 2*a* of the filling machine 2 by the operation of the actuator, and the front end of the drain pipe 20 is connected to the opening of each of the filling nozzles 2*a*.

Further, to the drink supply pipe line 7, there are provided the manifold valve 8, the actuator, not shown, various types of change-over valves, and pumps, which are also controlled by output of the controller 17.

Hereunder, the sterilizing method for the drink filling system of the structure mentioned above will be explained with reference to FIGS. 2 to 5.

(1) When operation buttons arranged on a panel, not shown, of the controller 17, the SIP treatments are performed to the upstream side pipe line section 7*a* and the downstream side pipe line section 7*b* of the drink supply pipe line 7 in accordance with predetermined sequence (see FIGS. 2 and 3). At the time of starting the SIP treatment, the connection between the upstream side pipe line section 7*a* and the downstream side pipe line section 7*b* is shut off by the operation of the manifold valve 8.

The SIP treatments for the upstream side pipe line section 7*a* and the downstream side pipe line section 7*b* may be performed in series or in parallel with each other.

(2) First, water is supplied from a water supply source, not shown, into a circulation path through the balance tank 5, and the water then circulates in the circulation path while being heated and sterilized by the UHT section 18, thereby sterilizing the interior of the upstream side pipe line section 7*a*.

(3) At the time when the hot water flows in the upstream side pipe line section 7*a*, the information of each temperature is sent from each of the temperature sensors 10 arranged at plural portions of the upstream side pipe line section 7*a* to the controller 17 for a predetermined constant time interval.

In the present embodiment, pH of a drink as product liquid filling a bottle b is set to be not less than 4.6, a reference temperature Tr is set to be 121.1° C. and a Z-value is set to be 10° C.

Figure 5:
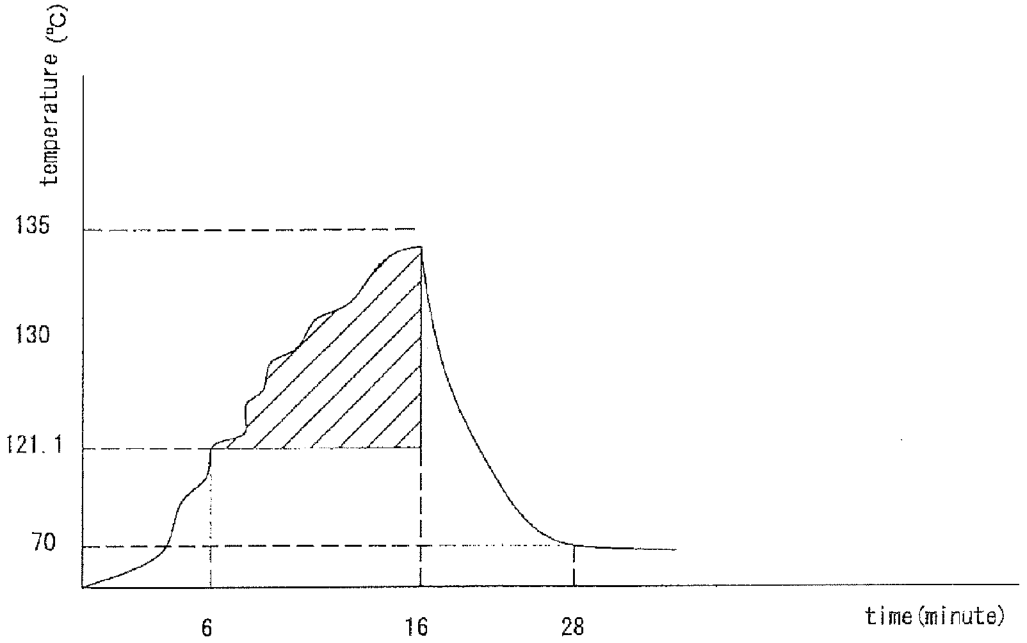
FIG. 5 is a graph representing a heating method for the drink supply pipe line with a relationship between temperature and time.

As shown in FIG. 5, at a time when the temperature at each portion increased by the heating of the hot water reaches 121.1° C., an F-value of each portion is calculated at that time point by the controller with the following arithmetic (calculating) equation.

$$F=\int_{t_0}^{t_1} 10^{(T-121.1)/10}dt \quad \text{[Equation 3]}$$

wherein T is an optional sterilizing temperature (° C.), $10^{(T-121.1)/10}$ is a fatality rate at the optional temperature T, which corresponds to a heating time (minute) at the temperature of 121.1° C., in which the value 121.1 is the reference temperature (C), and 10 represents the Z-value (9C).

At a time when the minimum F-value among the respective F-values calculated based on the above arithmetic equation reaches the aimed value, it is deemed that the sterilization process is ended, the cooling water is supplied to the first stage cooling section 15 and the second stage cooling section 16 to thereby cool the hot water, and the cooled hot water then circulates continuously till the time when the drink sterilization process starts.

The aimed value of the F-value corresponds to an area hatched in FIG. 5 concerning the temperature sensor 10 arranged at certain portion. The hatched area in FIG. 5 corresponds to an area hatched in FIG. 6.

Figure 6:
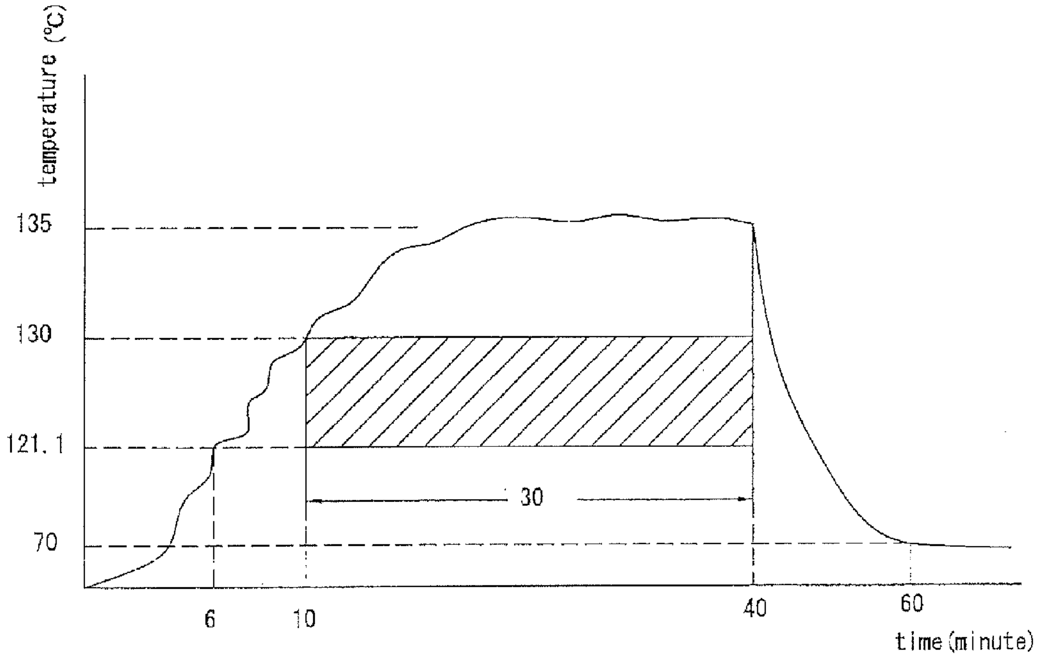
FIG. 6 is a graph representing a heating method for the drink supply pipe line with a relationship between temperature and time according to a conventional technology.

In a conventional technology, as shown in FIG. 6, a timer for detecting the fact of completion of the sterilization is operated at a time when all the temperature sensors indicate 130° C. and this fact is announced after 30 minutes later from the completion of sterilization. Moreover, before the temperature reaches 130° C., about 10 minutes have passed from the starting time of supplying the hot water or heated steam. On the contrary, with the present invention, the arithmetic calculation of the respective F-values is started at the time when the temperatures of all the sensors 10 reach 121.1° C., so that the time before the calculation starting can be shortened by 6 minutes. In addition, in the conventional technology, the heating sterilization is constantly performed for about 30 minutes from the arithmetic calculation starting time while feeding the hot water or heated steam, which results in the heat accumulation to the drink supply pipe line 7 and so on, and accordingly, about 20 minutes are required for the cooling. However, according to the present invention, cumulative calculation of the F-value is started after 6 minutes from the heating start time, which is shorter by 10 minutes, in the heating time, and less heat accumulation is applied to the drink supply pipe line 7 and so on, so that the time required for the cooling can be shorten by 12 minutes. Therefore, the time interval from the heating to the cooling can be remarkably shorten to 28 minutes compared with a conventional case in which 60 minutes is required for the cooling.

Further, in the above-mentioned arithmetic equation for the F-value, the reference temperature Tr and the Z-value may be changed in accordance with kinds of drinks as product liquids.

For example, the pH of the product drink is less than 4 to 4.6, the reference temperature Tr and the Z-value may be set to Tr=60° C. and Z-value=5° C.

Furthermore, values to be plugged in to the above arithmetic equation in conformity with bacteria growing characteristics, circulation temperature and the like of the product liquid such as green tea, mineral water, child drink or the like may also be optionally changed.

(4) Thereafter, the drink is delivered to the balance tank 5 from the preparation apparatus 1 and is then subjected to the sterilization treatment. At a timing when the water is converted into the drink, a portion in the pipe line between the upstream side pipe line section 7*a* and the return circulation path is shut off, and the sterilized drink is stored in the aseptic tank 19.

(5) At the same time or in advance of the starting of the SIP treatment for the upstream side pipe line section 7*a*, the SIP treatment starts to be performed to the downstream side pipe line section 7*b* inclusive of the aseptic tank 19.

First, the cups 9 are applied to the openings of the filling nozzles 2*a*, respectively, and the drain tubes 20 are connected to the filling nozzles 2*a*, respectively, and thereafter, the heated steam is supplied into the aseptic tank 19 and the head tank 11 from the heated steam supply source, not shown.

This heated steam flows from the aseptic tank 19 into the downstream side pipe line section 7*b*, and after the heating of the respective sections or the like, the heated steam is discharged outside the filling machine 2 through the drain tube 20.

(6) When the heated steam flows inside the downstream side pipe line section 7*b*, the temperature informations from the respective temperature sensors 10 arranged at various portions are reported with constant interval to the controller 17.

As shown in FIG. 5, the temperatures at the various portions increased by the heating of the heated steam reach 121.1° C., the F-values of these portions are arithmetically calculated, at this timing, based on the above-mentioned arithmetic equation by the controller 17.

At the time when the minimum F-value among the calculated respective F-values reaches the aimed value, the supply of the heated steam into the aseptic tank 19 and the downstream side pipe line section 7*b* stops. The aimed value of the F-value corresponds to the area hatched in FIG. 5. As can be seen from comparison result of the cases shown in FIG. 5 and FIG. 6, the time required for the SIP treatment in the downstream side pipe line section 7*b* can be remarkably shortened in comparison with the time for the conventional SIP treatment.

(7) Thereafter, the aseptic air is supplied into the downstream side pipe line section 7*b*, and the interior of the downstream side pipe line section 7*b* is then cooled to a temperature, for example, of room temperature. Thereafter, the drain tube 20 is shut off, and the cups 9 are removed from the openings of the filling nozzles 2*a*, respectively, by an actuator, not shown.

(8) The drink is stored into the aseptic tank 19 from the UHT section 18 through the upstream side pipe line section 7*a* after the completion of the SIP treatment for the downstream side pipe line section 7*b* as well as the aseptic tank 19, and the drink filling operation for filling the bottles 4 starts through the downstream side pipe line section 7*b*.

Figure 4:
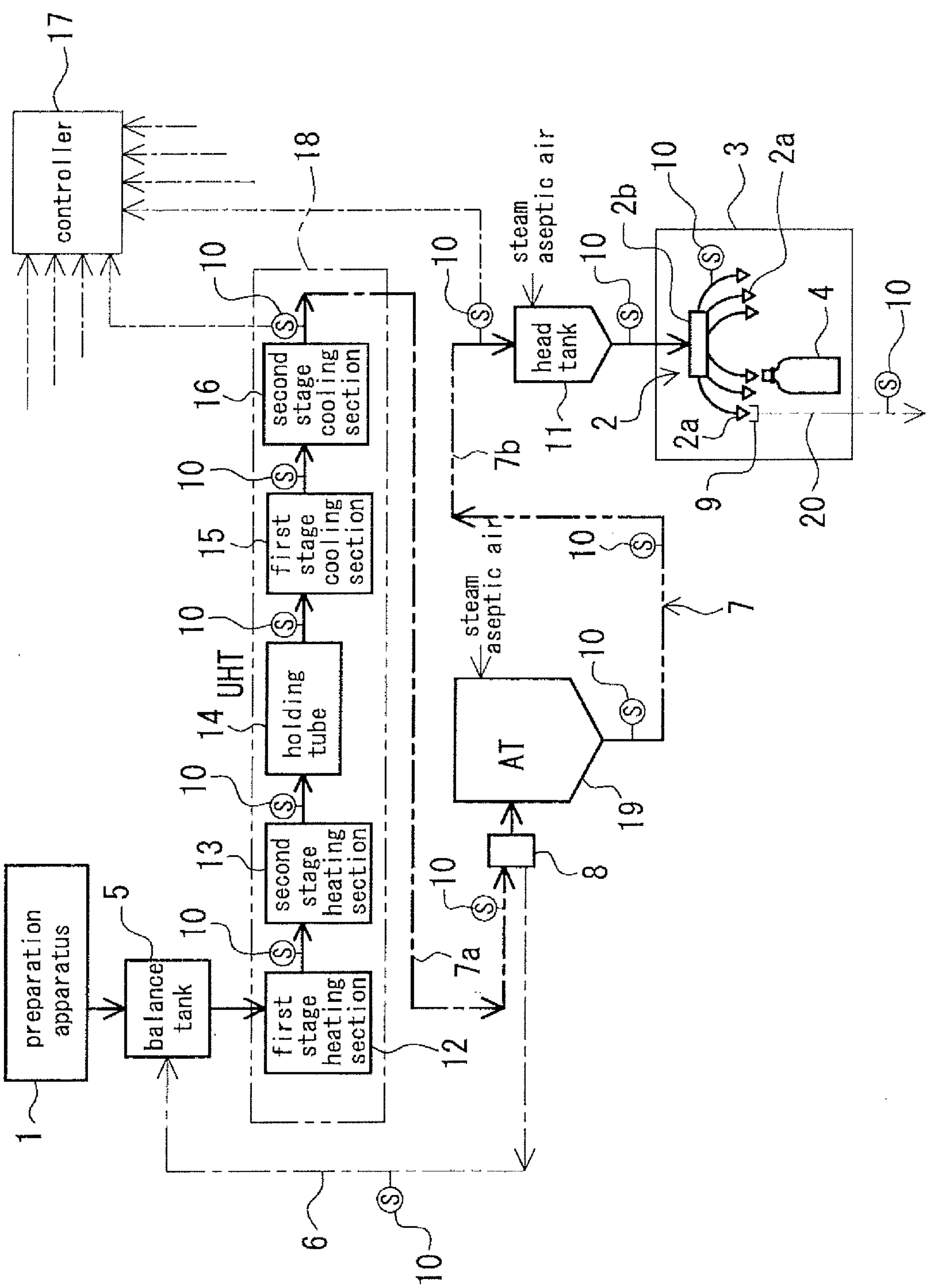
FIG. 4 is a block diagram sowing a state in which bottled products of the drink are produced.

As shown with the thick line in FIG. 4, the drink prepared in the drink preparation apparatus 1 is delivered into the filling machine 2 through the upstream side pipe line section 7*a* and the downstream side pipe line section 7*b* of the sterilized drink supply pipe line 7, and thereafter, the bottle 4 as a container is filled up with the drink through each of the filling nozzles 2*a* of the filling machine 2. The bottles 4 filled up with the drink are capped by a capper, not shown, and then fed out of the filling machine 2.

It is to be noted that although the present invention is constructed as explained hereinabove, the present invention is not limited to the embodiment described above, and many other changes and modifications may be made within the scopes of the present invention. For example, in the above-described embodiment, although the SIP treatment for the upstream side pipe line section and the SIP treatment for the downstream side pipe line section are performed by using different fluids such as hot water and heated steam, both the SIP treatments may be performed with the same kind of fluid. Furthermore, it may be possible to perform the SIP treatment by releasing the manifold valve so as to establish the communication between the upstream side pipe line section and the downstream side pipe line section to thereby flow the fluid from the upstream side pipe line section to the downstream side pipe line section. Still furthermore, the time interval for the measurement and accumulation of the F-value may be set to one-minute interval or one-second interval, and such time interval may be changed in accordance with ability or like of a measurement equipment to be used.

REFERENCE NUMERAL

2 - - - filling machine
6 - - - upstream side return path
7 - - - drink supply pipe line
7*a* - - - upstream side pipe line section
7*b* - - - downstream side pipe line section
18 - - - heat sterilizing section

The invention claimed is:

1. A sterilizing method for a drink filling system provided with a drink supply pipe line for feeding drink into a filling machine through a heat sterilizing section, wherein hot water or heated steam is fed to the drink supply pipe line, F-values are calculated while detecting temperature of the fluid within the pipelines at a plurality portions of the drink supply pipe line at every predetermined time interval, and a sterilizing process is ended at a time when a minimum F-value reaches an aimed value, wherein an upstream side return path is provided for the upstream side pipe line section going through the heating sterilizing section of the drink supply pipe line to thereby form an upstream side circulation path, the F-values are calculated while flowing the hot water from the upstream side pipe line section and flowing the heated steam toward the inside of the filling machine from the downstream side of the upstream side pipe line section, and the sterilizing process is ended at a time when each of the minimum F-values reaches the aimed valve.

2. The sterilizing method for a drink filling system according to claim 1, wherein the F-value is calculated by using a following equation 1:

$$F=\int_{t_0}^{t_1} 10^{(T-Tr)/Z}dt \quad \text{[Equation 1]}$$

wherein T is an optional sterilizing temperature (° C.), $10^{(T-Tr)/Z}$ is a fatality rate at the optional temperature T, which corresponds to a heating time (second) at the temperature of 121.1°, in which the value 121.1 is the reference temperature (° C.), and 10 represents the Z value (° C.).

3. A drink filling system provided with a drink supply pipe line for feeding drink into a filling machine through a heating sterilizing section, wherein hot water or heated steam is fed to the drink supply pipe line, F-values are calculated while detecting temperature of the fluid within the pipelines by temperature sensors disposed at a plurality portions of the drink supply pipe line at every predetermined time interval, and a sterilizing process is ended at a time when a minimum F-value reaches an aimed value, wherein an upstream side return path is provided for the upstream side pipe line section going through the heating sterilizing section of the drink supply pipe line to thereby form an upstream side circulation path, the F-values are calculated by temperature sensors disposed at predetermined portions of the upstream side circulation path while flowing the hot water in the upstream side circulation path and the F-values are calculated also by temperature sensors disposed at predetermined portions of the downstream side circulation path while flowing the heated steam to the downstream side pipe line section extending from the upstream side of the upstream side pipe line section towards the inside of the filling machine, and the sterilizing process is ended at a time when each of the minimum F-values reaches the aimed valve.

* * * * *